US009974805B2

United States Patent
Strothmann et al.

(10) Patent No.: US 9,974,805 B2
(45) Date of Patent: May 22, 2018

(54) PHOSPHATE BINDER FORMULATION FOR SIMPLE DOSING

(71) Applicant: Fresenius Medical Care Deutschland GmbH, Bad Homburg (DE)

(72) Inventors: Kai Strothmann, Wuerselen (DE); Friedrich Schulze, Neu-Anspach (DE); Johannes Bartholomaeus, Aachen (DE); Eva Fries-Schaffner, Bad Vilbel (DE); Astrid Bonert, Frankfurt am Main (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days. days.

(21) Appl. No.: 15/144,138

(22) Filed: May 2, 2016

(65) Prior Publication Data

US 2016/0243160 A1    Aug. 25, 2016

Related U.S. Application Data

(62) Division of application No. 13/879,479, filed as application No. PCT/EP2011/005069 on Oct. 11, 2011.

(30) Foreign Application Priority Data

Oct. 13, 2010  (EP) ..................................... 10013578

(51) Int. Cl.

| A61K 33/10 | (2006.01) |
|---|---|
| A61K 9/46 | (2006.01) |
| A61K 9/00 | (2006.01) |
| A61K 9/16 | (2006.01) |
| A61K 31/77 | (2006.01) |
| A61K 33/06 | (2006.01) |
| A61K 31/19 | (2006.01) |
| A61K 31/225 | (2006.01) |
| A61K 31/7004 | (2006.01) |

(52) U.S. Cl.
CPC ............ *A61K 33/10* (2013.01); *A61K 9/0007* (2013.01); *A61K 9/0056* (2013.01); *A61K 9/1617* (2013.01); *A61K 9/1635* (2013.01); *A61K 9/1652* (2013.01); *A61K 31/19* (2013.01); *A61K 31/225* (2013.01); *A61K 31/7004* (2013.01); *A61K 31/77* (2013.01); *A61K 33/06* (2013.01)

(58) Field of Classification Search
None
See application file for complete search history.

(56) References Cited

U.S. PATENT DOCUMENTS

| 5,312,626 | A | | 5/1994 | Gergely et al. |
|---|---|---|---|---|
| 5,639,475 | A | * | 6/1997 | Bettman .............. A61K 9/0007 424/441 |
| 7,465,465 | B2 | | 12/2008 | Haslam et al. |
| 2001/0018082 | A1 | | 8/2001 | Fox |
| 2006/0121127 | A1 | | 6/2006 | Ferdinando et al. |
| 2007/0059277 | A1 | | 3/2007 | Bhagat et al. |
| 2013/0202699 | A1 | | 8/2013 | Strothmann et al. |

FOREIGN PATENT DOCUMENTS

| CN | 1820739 | 8/2006 |
|---|---|---|
| CN | 101378767 | 3/2009 |
| DE | 202008015620 | 1/2010 |
| EP | 0424706 | 5/1991 |
| EP | 0525388 | 2/1993 |
| EP | 1270001 | 1/2003 |
| EP | 1924246 | 5/2008 |
| EP | 2161022 | 3/2010 |
| EP | 2441436 | 4/2012 |
| WO | WO 2005/018651 | 3/2005 |
| WO | WO 2007/054782 | 5/2007 |
| WO | WO 2007/088343 | 8/2007 |
| WO | WO 2008-011126 | 1/2008 |

OTHER PUBLICATIONS

Delmez et al. (Kidney International 49, 163-167, 1996) Magnesium Carbonate as a phosphorous binder . . . .*
Emmett (Dialysis & Transplantation, 1-8, 2006) A comparison of calcium based . . . .*
European Search Report dated Apr. 15. 2016.
Bricker et al. (JAMA Network_JAMA Internal Medicine, 13(5), 1969, abstract.
Definition of characterize. Oxford English Dictionary, Accessed Jun. 1, 2015.
Chiu et al. Pill Burden, Adherence, Hyperphophatemia, and Quality of Life in Maintenance Dialysis Patients. Clin J Am Soc Nephrol 4: 1089-1096 2009.
Bayraktar et al. Evaluation of salivary parameters and dental status in adult hemodialysis patients. Clinical Nephrology, vol. 62, No. 5, 2004 (380-383).
Arenas et al. A comparative study of 2 new phosphate binders-(sevelamer and lanthanum carbonate) in routine clinical practice. JN Ephrol 2010; 23(06): 683-692.
Lindberg et al. Overcoming obstacle for adherence to phosphate binding medication in dialysis patients: a qualitative study, Pharm World Sci (2008) 30:571-576.

* cited by examiner

*Primary Examiner* — Tigabu Kassa
(74) *Attorney, Agent, or Firm* — Jacobson Holman, PLLC.

(57) ABSTRACT

The invention relates to a pharmaceutical composition in the form of pourable granules or a chewable tablet containing at least one phosphate binding substance and at least one effervescent agent. The composition may be taken orally without adding water.

8 Claims, No Drawings

PHOSPHATE BINDER FORMULATION FOR SIMPLE DOSING

INITIAL SITUATION AND STATE OF THE ART

The invention relates to pharmaceutical compositions containing phosphate binders, which may be taken orally without adding water. The pharmaceutical composition here is preferably in the form of granules or a chewable tablet containing an effervescent agent.

Renally insufficient patients and dialysis patients in particular often suffer from a hyperphosphatemia requiring treatment. Hyperphosphatemia is a pathophysiological elevation in the blood phosphate level. Hyperphosphatemia occurs with a massive intake of phosphate, massive release of phosphate due to tissue destruction, reduced phosphate elimination in advanced renal failure and/or conditions with an increased phosphate resorption through the kidneys. The rise in serum phosphate may lead to deposition of calcium phosphate in blood vessels and other tissues. Chronic hyperphosphatemia can lead to calcification of tissues and blood vessels, which may result in circulation disorders, myocardial infarction and/or a stroke. Therefore renally insufficient patients must usually take phosphate binders to control their serum phosphate levels. The phosphate binders should be taken with meals to bind the phosphate contained in food in the form of sparingly soluble salts or unabsorbable complexes in the intestine and therefore eliminate them with the feces. To do so, the patients must take a large quantity of the phosphate binder, usually in the form of a large number of tablets, for example, 1 to 5 tablets three times daily with each meal. To be able to take large quantities more easily or with fewer labels, it is either necessary to take an even larger number of tablets in the case of smaller tablets or much larger tablets that are more difficult to take may be administered in the case of fewer tablets. However, this large number of tablets is only a portion of the total oral medication taken by a renally insufficient patient. In a recent study on 233 dialysis patients, they were taking an average of 11 different medications, resulting in 19 tablets to be taken per day as the median (Chiu, Y. W. 2009). Of these, approximately 50% were phosphate binders.

In addition, renally insufficient patients and in particular dialysis patients are allowed to drink only a small amount of water per day, so that the tablets cannot be swallowed easily. Renally insufficient patients cannot eliminate excess fluid from the body via the urine or can do so only to a limited extent. Therefore, most renally insufficient patients suffer from a permanent fluid excess in the body which has a negative influence on their well-being as well as their mortality. Excess fluid can cause hypertension, which can damage the cardiovascular system and in particular the function of the left ventricle and thus can contribute indirectly toward an increased mortality of renally insufficient patients due to cardiovascular diseases. Furthermore, a large percentage of renally insufficient patients suffer from anemia and receive hematopoietic medication in the form of Epogen or analogs and in the form of iron preparations. A fluid excess reduces the concentration of the hematopoietic medications and thus makes suitable dosing of these medications much more difficult. Therefore, control of fluid intake is extremely important in renally insufficient patients. In most cases, the goal is to minimize fluid intake in renally insufficient patients.

This is complicated by the fact that dialysis patients have approximately half as much saliva as healthy control groups (Bayraktar, G., 2004). Compliance in taking medication is therefore influenced in a negative sense. In contrast with the number of different medications prescribed, the number of phosphate binder tablets prescribed must be seen in conjunction with patient compliance in particular (Arnas, M. D., 2010). If dialysis patients are asked which medication they would most prefer to omit if they had a choice, phosphate binders would be listed in first place (Arenas, M. D. 2010). An improved dosage form that is patient friendly and better-tasting phosphate binders would make a significant contribution toward meeting patients' requests (Lindberg, M., 2008).

U.S. Pat. No. 7,465,465 discloses chewable tablets with lanthanum as a phosphate binder which must be chewed before swallowing to remedy these problems. This may be difficult for a dialysis patient who has reduced saliva. Crushing the tablet and then distributing it on food or a spoon is associated with the risk of taking too little of the active ingredient because of losses in preparation and/or incomplete ingestion of the foodstuff.

EP 1 924 246 discloses powder preparations with a suspension stabilizer for taking the powder after suspending it in water. This is associated with the disadvantage of the larger quantity of water of the suspension against the water restrictions for dialysis patients. It is customary to suspend such a powder in at least 40 mL-60 mL water before it is taken. Thus the total quantity of water ingested adds up to approximately 120-300 mL per day for administration of the phosphate binder alone. To supply the total dose of the phosphate binder more reliably, it is also necessary to use more water to rinse off the powder particles adhering to the edge, which remain on the glass wall after taking the suspension and then to also drink this water.

To reduce the water ingested with the phosphate binder, WO 2008/011126 discloses concentrated solutions of calcium acetate with large quantities of polyols, sweeteners and taste-masking substances. In such formulations, a portion of the bad inherent taste of calcium phosphate remains perceptible overall on the one hand, and on the other hand, a number of patients reject the intense, always uniform taste of the sweeteners and flavorings, which do not correspond to all meals. For combination products with readily water-soluble calcium acetate and sparingly soluble magnesium carbonate, there is the additional disadvantage of dosing inaccuracy because it is difficult to dose magnesium in suspended form by means of a dropper, etc.

All the approaches toward simpler dosing described here have the additional disadvantage that in any case the product is distributed involuntarily in wide areas of the oral cavity, producing an unwanted taste. This taste becomes more intense when parts of the product remain in parts of the oral cavity for an even longer period of time.

Therefore, the object of the invention is to make available a dosage form for phosphate binders that will allow renally insufficient patients to easily take the required large quantities of phosphate binders without any additional quantities of water. In a second aspect, the dosage forms should mask any poor taste of the phosphate binder and should impart a pleasant feel in the mouth. In another aspect the object of the invention is to make available a composition which will be distributed involuntarily in the oral cavity as little as possible and will allow accurate doing.

These objects are achieved through the composition according to Claim 1 and its application as well as through the subject matters of the additional independent claims.

Additional objects are achieved by preferred embodiments of the invention which are the subject matter of the dependent claims.

A pharmaceutical composition in the form of pourable granules or a chewable tablet containing at least one phosphate binding substance and at least one effervescent agent which in turn contains an alkali carbonate or an alkaline earth carbonate or an alkali bicarbonate or alkaline earth bicarbonate and a solid organic edible acid or the acid salt thereof is used in the treatment of renally insufficient patients and is characterized in that the granules are administered orally without adding water or another liquid and can then be swallowed. In this way, the medication can be taken without any additional intake of fluid. Washing it down with water is not absolutely ruled out but is not necessary. It is decisive that the composition is taken first in the mouth without water. The effervescent agent has the effect of masking the taste and imparts a pleasant feeling in the mouth. In this way, the pharmaceutical composition can be partially dissolved in saliva and swallowed mostly completely by the tongue.

The pharmaceutical composition is ideally administered from a stickpack directly to the tongue. In the case of an active ingredient with a bad taste, it may additionally be coated in the granules to mask the taste if a simple flavoring and/or the effervescent agent is not sufficient to mask the taste.

Phosphate binders are substances which interact with phosphate ions including crotonated phosphate ions and thereby hinder them in being taken up from the gastrointestinal tract into the blood stream and thus into the body to ensure the elimination of phosphates in the feces.

Phosphate binders that may be used include in particular calcium, magnesium, aluminum, iron, lanthanum and bismuth salts, whose solubility products are larger than those of the corresponding phosphate salts of these cations. In addition, phosphate-binding organic polymers having an anion exchanger function such as sevelamer, AMG 223 (Amgen) and MCI-196 (Colestilan, Mitsubishi) are suitable substances for the invention. Suitable aluminum salts include all the pharmaceutically tolerable salts which fulfill the above requirements, especially preferably oxides, in particular algedrate and/or hydroxides. All the pharmaceutically acceptable salts which fulfill the above requirements, in particular lanthanum carbonate including its hydrates are suitable as the lanthanum salts. All the pharmaceutically acceptable salts which fulfill the above requirements, preferably chlorides, sulfates, hydroxides, oxides, carbonates and in particular heavy magnesium carbonate are suitable as the magnesium salts. Preferred phosphate binders based on metal salts include iron hydroxides, iron oxide hydroxides and iron citrates, in particular iron preparations, which are stabilized by carbohydrates or humic acid or are bound to them or form sheet salts with magnesium, for example, fermagates and calcium salts, preferably calcium carbonate and/or calcium chloride and especially preferably calcium acetate. Calcium acetate is preferred in comparison with calcium carbonate because of its high solubility but it has the disadvantage of an extremely unpleasant taste. Of the metal salts, calcium salts are especially good phosphate binders and have a favorable price. However, as a disadvantage it is discussed that calcium preparations can cause hypercalcemia in many patients, i.e., elevated blood calcium levels. Chronic hypercalcemia is associated with the risk of calcification of the blood vessels and thus in turn with the risk of cardiovascular diseases. Replacing some of the calcium in such phosphate binders with magnesium which itself functions as a phosphate binder reduces the risk of development of hypercalcemia. It has been demonstrated that by adding magnesium salts, in particular magnesium carbonate to phosphate binding calcium acetate, hypercalcemia and therefore calcification can be largely prevented and no negative effects can be detected in comparison with patients treated with calcium-free phosphate binders (de Francisco, A. L. M. et al., Nephrol Dial Transplant 2010). To achieve this effect, a preferred weight ratio of calcium acetate to magnesium carbonate of 1:1 to 4:1 is assumed, but a ratio of 1.2:1 to 3:1 is especially preferred and a ratio of 1.5:1 to 2:1 is most especially preferred. Magnesium salts also have an independent phosphate binding effect, so that in the presence of magnesium salts, the quantity of phosphate binder based on calcium required can be reduced. A combination of calcium acetate and magnesium carbonate thus constitutes an especially preferred composition in the sense of the present invention. Another special advantage of this combination is derived from the fact that magnesium carbonate is also a preferred ingredient of the effervescent agent inasmuch as magnesium carbonate can fulfill two functions at the same time within the composition. The weight and the volume of the composition per dose to be taken by the patient are further reduced in this way. A daily dose ideally contains 100 mg to 3000 mg calcium and 0 mg to 1500 mg magnesium abased on the weight of the metal ions, but 300 mg to 1800 mg calcium is preferred and 180 mg to 750 mg magnesium, 450-1350 mg calcium and 180-540 mg magnesium being most preferred. In the absence of magnesium, the preferred quantities for calcium are increased by a factor of 1.5.

For ion exchange polymers, in particular sevelamer, the ideal daily dose is 500-12,000 mg preferably 2000-10,000 mg and especially preferably 5000-8000 mg.

For phosphate binders based on lanthanum, the ideal daily dose based on lanthanum is 250-5000 mg preferably 750-4000 mg, 1500-3000 mg.

The daily dose is usually divided among 3 to 15 individual doses to be taken with each meal. It is customary to take 1 to 4 individual doses with the three main meals per day.

Because of the large quantity in which phosphate binders must still be taken, one goal of the present invention is to minimize the weight and the volume of the final composition. The admixture of other excipients should be limited to a minimum. The composition according to the invention preferably contains 15% to 80% of the phosphate binding active ingredient, especially preferably 20% to 70% and most especially preferably 25% to 60%.

All the aforementioned phosphate binders must be taken in large quantities and the object of the present invention is to make it possible for these quantities to be taken without additional intake of fluid. Tablets of this size or capsules containing the active ingredient are virtually impossible to swallow without taking some fluid at the same time. The only remaining options are a chewable tablet or granules. For both dosage forms it is of crucial importance for the dosage form to taste good and to impart a pleasant feeling in the mouth because both dosage forms have a large surface area in the mouth when taken and have the potential to distribute themselves throughout the entire mouth. An unpleasant taste or an unpleasant feeling in the mouth is thus perceived especially strongly with these dosage forms. All the aforementioned phosphate binders in the form of granules or a chewable tablet that disintegrates in the mouth impart an unpleasant "chalky" or "sandy" feeling in the mouth and in particular impart a dry feeling. The dry feeling in the mouth is further exacerbated in renally insufficient patients who often suffer from a lack of saliva. Furthermore, some of the active ingredients, for example, calcium acetate have a very unpleasant inherent taste.

According to the invention, an effervescent agent is therefore added to the composition. The effervescent agent is dissolved by saliva in the mouth, thereby releasing carbon dioxide in a chemical acid-base reaction. The carbon dioxide thereby released stimulates additional formation of saliva, especially in cooperation with flavorings and is also perceived as fresh and pleasant in the mouth. Due to the increased salivation, the feeling of dryness disappears and the composition can be swallowed more easily after being mixed with saliva. In addition, the carbon dioxide thereby released has a taste-masking effect per se.

The effervescent agent contains at least one solid organic edible acid and/or its salt and at least one salt which released carbon dioxide, in particular a carbonate, preferably selected from the group of alkali salts and alkaline earth salts and their metal hydrogen salts. Especially suitable are sodium carbonate, sodium bicarbonate, potassium carbonate, potassium bicarbonate, magnesium carbonate and/or calcium carbonate. Magnesium carbonate is especially preferred because in addition to the effervescent function it also acts as an active ingredient against hypercalcemia and has phosphate binding properties. Calcium carbonate is also preferably used because the calcium supplied in the effervescent agent has a phosphate-binding effect and thus makes it possible to reduce the amount of active ingredient. The effervescent reaction also counteracts the disadvantage of the low solubility of calcium carbonate. Suitable acids include in particular citric acid, tartaric acid, malic acid, adipic acid, succinic acid, fumaric acid, ascorbic acid, maleic acid and ascorbic acid as well as partial salts of these acids in the case of polybasic acids, for example, monosodium tartrate. Such acids, which additionally stimulate salivation and/or have a pleasant inherent taste, are also especially preferred to facilitate swallowing of the slightly foaming preparation and also to improve the taste of the composition. Tartaric acid, citric acid, ascorbic acid, sodium and potassium tartrate, sodium hydrogen citrate and sodium ascorbate are especially suitable for this purpose.

The effervescent formulations according to the invention may be produced by conventional methods that are known in the state of the art. For example, the acids and carbonates are granulated separately, preferably by moist granulation, during which the active ingredients are added to one of the granules. After mixing, soluble lubricants such as sodium benzoate or polyethylene glycols are added to the carefully dried granulates and compressed. According to another method, all acids, carbonates and active ingredients are mixed together and heated in a reactor until the citric acid releases its water of crystallization, for example, and granules are formed. Repeated stirring is necessary to obtain a uniform composition, which is then screened rapidly and dried carefully. Good drying is absolutely essential to avoid gradual disintegration of the granules due to reaction of the acids with the carbonates. To achieve rapid drying, for example, vacuum drying cabinets or so-called one-pot granulators with vacuum-assisted drying are used. In another variant of production, the initial reaction of the acid with basic components and subsequent drying takes place in a vacuum. The resulting effervescent granules according to the invention are pressed with additional ingredients of the composition to form chewable tablets or are packed into stickpacks. The dosage of the effervescent formulation plays an important role for the invention. On the one hand enough effervescent agent must be present to permit a perceptible release of carbon dioxide which produces the pleasantly fresh feeling in the mouth and masks the taste. On the other hand the composition should not foam too much in the mouth because most patients do not perceive this as pleasant. The proportion of effervescent agent in the composition is therefore ideally 3-60% of the total weight, preferably 5-45% and especially preferably 10-30%.

There are various methods with which those skilled in the art are familiar which make it possible to incorporate phosphate binding active ingredients into granules. The active ingredient here, optionally with the addition of excipients, is preferably itself in the form of granules which represent the final granulated composition or are a component thereof. On incorporation into granules, both pregranulated active ingredients and powdered active ingredients which are then granulated in subsequent steps may be used. The dosage forms may contain excipients which are bound into the granular structure as well as being added in the form of a powder to the particles of granules. The excipients used may include in particular fillers, sweeteners, acidifying agents, flavorings, coating agents, flow regulating agents and parting compounds. Granulation methods that may be used include in particular moist granulation, dry granulation and melt granulation, although other methods are not ruled out. In moist granulation, aqueous methods are preferred for environmental reasons and for reasons of occupational safety, but methods using organic solvents are also possible. For moist granulation and melt granulation, fluidized bed methods and high speed mixer methods are preferred (e.g., Diosna mixer or Granumat from Bohle) but alternative methods are also possible. Granulation methods which yield the densest possible granules to reduce the volume of the dose taken are preferred. In addition granules having a smooth surface with little porosity, which permit uniform moistening by saliva and impart a pleasant feeling in the mouth due to their smoothness are also preferred. Preferred granulation methods include moist granulation of the active ingredients with binders and subsequent drying in a fluidized bed and melt granulation.

In preferred embodiments, additional advantageous excipients are added to the active ingredient in granulation. Various excipients—such as fillers, parting compounds, binders, disintegrants, flow regulators, sweeteners and/or flavorings—are used for technical and pharmaceutical reasons in granulation and are very familiar to those skilled in the art. However, within the scope of the present invention, the excipients also ideally contribute toward improving the feeling in the mouth and the taste of the granules.

The fillers may be all pharmaceutically conventional tablet and granular fillers in particular inert compounds such as celluloses, starches and/or lactose. Sugars such as sucrose, glucose or fructose which improve the taste of the formulation and thus function as sweeteners at the same time are preferred within the scope of this invention. Sugar alcohols are especially preferred because they mask the unpleasant taste of the active ingredients with a pleasantly sweet inherent taste while on the other hand being easy to moisten with saliva. This leads to the desired effect of increased salivation and contributes toward a pleasant cool feeling in the mouth. Within the scope of the present invention, sugar alcohols may preferably be selected from the group comprising mannitol, inositol, erythritol, lactitol, xylitol, maltitol, malbitol, sorbitol, inulin and isomalt.

The sugar alcohols mentioned above may also be used as preferred binders in melt granulation. Other preferred binders within the scope of the invention in granulation with taste-masking properties at the same time include: cyclodextrin, alginic acid, Eudragit E-100, polacrilin, microcrystalline cellulose, beeswax, glycerol esters, triglycerides, polyglycerol esters of long-chain fatty acids, PEG, fatty alcohol PEG esters, fatty alcohol PEG ethers, PVP and derivatives, polyacrylic acid, polyacrylates, polymethacrylates and any combinations thereof. Low-melting binders which allow granulation at low temperatures and binders which are simultaneously hydrophilic or even to form hydrogels are especially preferred because they impart a better feeling in the mouth.

Sweeteners, e.g., aspartame, saccharine, cyclamate, acesulfam, neohesperidine, trehalose, alitame, dihydrochalcone, thaumatin and sucralose may also be used for additional sweetening because these sweeteners can also stimulate salivation in addition to having a sweetening effect.

In addition to a simple sweetening, flavorings and taste-improving substances are used to mask the taste, to produce a pleasant taste and to increase salivation. Fruit aromas and especially preferably citrus fruit aromas are preferred here because these impart an especially fresh taste and a cool feeling in the mouth. For the same reasons, mint flavorings are also preferred.

Flow regulators that may be used include those substances which allow an easy and uniform flow of the granules such as in particular highly disperse silicon dioxide, precipitated silicon dioxide and talc.

Fatty acids and their salts, e.g., stearic acid, magnesium stearate, calcium stearate, behenic acid and calcium behenate, fatty alcohols, e.g., stearyl alcohol, fats, e.g., hardened triglycerides and hardened castor oil, sodium fumaryl stearate, polyethylene glycol with a molecular weight of >1500 Dalton as well as talc are suitable parting compounds.

In another preferred embodiment, the active ingredient granules are coated with a substance to mask the taste. Those skilled in the art are familiar with many coatings and coating methods for taste-masking coatings. For example, the following materials are suitable for taste-masking coatings in the sense of this invention:

Cellulose acetate or cellulose acetate butyrate with PVP, Eudragit RD 100 with carboxymethyl cellulose, polyvinyl alcohol and polyethylene glycol copolymer, Eudragit 100 and PVP, polyvinyl acetate and pharmaceutically acceptable hydrophilic polymers, Eudragit E100 and pharmaceutically acceptable acids, polyacrylates, polymethacrylates, polymethacrylic eaters, combinations of enteric polymers with hydrophilic gel-forming polymers such as polyvinyl acetate or polyvinylpyrrolidone (PVP).

The preferred coating method is spray coating in a fluidized bed. In principle, both top spray and bottom spray methods are customary here. The bottom spray method is preferred here for coating particles and granules thereof. Typical representatives of devices in this field include those available from the following companies: Glatt, Aeromatic, Diosna and Bohle. A so-called Wurster insert is preferred for the bottom spray method. Another preferred type of bottom spray fluidized coating device is the ball coater and/or those from the Mycrolab, Unilab, Pilotlab family and/or HDGC from the company Oyster Hüttlin. As those skilled in the art are aware, in all these systems the coating is performed by spraying a solution of suspension of a polymer in water and/or another organic solvent is applied by means of a nozzle to a fluidized bed of particles and/or granules or pellets, where the fluidized bed is produced by introducing air, usually heated, and then drying.

In addition to traditional methods in which the coating is dissolved in water or an organic solvent and then dried in a fluidized bed, the melt coating method is considered and is especially preferred. In the melt coating method, low melting binders are used, additional substances being dissolved or suspended in their melt. The melt is sprayed in the fluidized bed and the coating hardens on cooling. Ideally binders which themselves have a taste-masking effect and cause a pleasant perception in the mouth are used, for example, lipophilic substances selected from the group of lipids, waxes, glycerol esters, triglycerides, polyglycerol esters of long-chain fatty acids, PEG, fatty alcohol PEG esters, fatty alcohol PEG ethers and PVP and derivatives, polyacrylic acids and polyacrylates, polymethacrylates and combinations thereof. Low-melting binders which allow granulation at low temperatures and binders which are hydrophilic at the same time or even tend to form hydrogels are especially preferred because this imparts a better feeling in the mouth.

A surface modifier which produces a smooth surface that is easy to moisten and thus additionally improves the feeling in the mouth is preferably added to the coating. Examples of surface modifiers include sorbitan fatty acid esters, polyoxyethylalkyl esters, polyoxyethylalkyl ethers, polyoxyethyl sorbitan fatty acid esters, polyoxyethyl stearates and copolymers thereof.

If a taste-masking coating is used within the scope of the present invention, then the effervescent agent should essentially not be present in the active ingredient granules because the taste-masking coating would prevent moistening of the effervescent agent by saliva on the one hand and would thus delay the release of carbon dioxide while on the other hand any carbon dioxide that might be formed could at least partially break open the taste-masking coating. In such a case the effervescent agent may be added in the form of additional granules or as a powder to the composition. In another embodiment, the effervescent agent may be present in the outer layer of the coating. This may be the same layer as the taste-masking coating or an additional layer.

The same thing also applies to sweeteners and flavorings which cannot manifest their taste-improving properties in the core of the coated active ingredient granules as for the effervescent agent. Sweeteners and flavorings are also preferably added in the form of additional granules or as a powder, where these may be the granules containing the effervescent agent or they may especially preferably be part of an outer coating.

The composition may be supplied in the form of free-flowing granules or a chewable tablet. The chewable tablet offers the advantages of ease of administration and accurate doseability as a tablet. Nevertheless within the scope of the invention, the pourable granular form is preferred. One reason for this is that the chewable tablet must be chewed. Therefore taste-masking coatings, for one thing, may be destroyed and for another thing chewing produces a large volume distribution in the mouth and may result in the substance sticking to the teeth, which makes rapid and complete swallowing difficult. The granules may be applied directly to the tongue and dissolved there, resulting in a comparatively minor distribution of the particles in the mouth between the tongue and gums and the granules can be swallowed completely. Within the scope of the invention, it has been found that particles with an average particle size of 100-3500 μm preferably 250-2500 μm and especially preferably 400-2000 μm are perceived as being especially pleasant for this application. (The average particle size can be determined by the shaking screen method according to DIN 53477.) Particles of this size are often combined in the mouth to form a particularly pasty consistency which is easy to swallow. Larger particles prevent this advantageous pasty consistency from being formed whereas smaller particles in the mouth are perceived as dusty. Smaller particles because of their larger total surface area adsorb more saliva so more saliva is needed for initial dissolving, which promotes the unwanted effect of dryness in the mouth.

The phosphate binder in a daily total dose of 40-10,000 mg may be packaged as a single dose or as multiple doses. The daily dose should be divided among meals, usually three, and taken with meals. The precise dosing is preferably adjusted according to the patient's phosphate levels in the course of treatment. It is thus advisable to package the most common dose per meal in individual packages. Patients having a low demand for phosphate binders would then take less than the total contents of one package per meal or would divide the contents of one package among several meals. Patients having a high demand could take more than the contents of one package.

For a phosphate binder based on calcium, preferably 70-700 mg calcium and 0-300 mg magnesium, based on the weight of the metal ions, preferably 100-450 mg calcium and 50-240 mg magnesium and most especially preferably 150-300 mg and 80-160 mg magnesium are packaged individually.

For a phosphate binder based on an ion exchanger, preferably 150-3000 mg of the active ingredient, preferably 300-2500 mg and most especially preferably 600-1700 mg are packaged individually.

For a phosphate binder based on lanthanum, preferably 40-1000 mg lanthanum, based on the weight of the metal ions, preferably 50-750 mg and most especially preferably 80-500 mg is packaged individually.

Suitable packages for the preparations according to the invention in the form of granules include in particular packages containing the dose of phosphate binder to be administered and from which the preparation can be applied directly to the mouth, preferably to the tongue. A bag package, especially preferably a so-called stickpack package in which the preparation is enclosed in a tubular package, is preferred. The tubular package is preferably produced by placing the material, preferably a film, around a round guide sleeve and connecting it at the sides of the material that come in contact. The resulting tube is sealed at its lower end, filled with the preparation which is then preferably dosed through the guide sleeve and then sealed at its upper end. In the case of a film tube, the welding of the upper part of the package preferably takes place together with the welding of the lower part of the following package and the separation of the two packages. After being cut or torn open on a short side of the bag, the stickpack has a small opening of preferably less than 1 cm diameter out of which the preparation can be administered into the mouth out of the bag, preferably following gravity. The granules pour out of the package into the mouth and the granules may be supplied in portions in the case of larger filling quantities in the bag. Smaller filling quantities may be administered all at once as a bulk dose.

The filling quantity of a stickpack is based on the quantity which contains an adequate amount of the active ingredient on the one hand and on the other hand the quantity that is still perceived as pleasant by the patient when taking it in the mouth. Such a stickpack therefore preferably contains 0.5-8 g of the total composition; especially preferably the stickpack contains 0.75-5 g of the composition, and most especially preferably 1-3.5 g.

EXAMPLES

Example 1

A granular preparation containing 110 mg calcium and 60 mg magnesium per dose can be prepared by the following method:

| | |
|---|---|
| Calcium acetate (according to the requirements of the European Pharmacopoeia)* | 435 g |
| Heavy magnesium carbonate (according to the requirements of the European Pharmacopoeia) | 235 g |
| Mannitol | 338 g |
| Sodium bicarbonate | 67 g |
| Monosodium dihydrogen citrate | 67 g |
| Citric acid | 13 g |
| Aspartame | 5 g |
| Orange flavoring | 30 g |
| Highly-disperse silicon dioxide | 10 g |

*For anhydrous calcium acetate, for hydrated calcium acetate, the initial weight must be adjusted, based on the water content and more calcium acetate must be added. This step must be taken into account for all examples using calcium acetate.

Calcium acetate, heavy magnesium carbonate, sodium hydrogen phosphate and 75% of the mannitol are converted to granules by roller compacting and subsequent screening for a 1.5 mm screen.

Monosodium hydrogen citrate, citric acid and the remaining 25% of the mannitol are also converted to granules by means of roller compacting and then screening through a 1.5 mm screen.

Granules, aspartame, orange flavoring and highly disperse silicon dioxide are mixed in a container mixer and then packaged in stickpacks with a filling weight of 1200 mg each.

Example 2

A granular preparation with 110 mg calcium and 60 mg magnesium per dose can also be prepared by the following method:

Effervescent Granules:

| | |
|---|---|
| Citric acid | 75 g |
| Monosodium citrate | 75 g |
| Sodium bicarbonate | 150 g |
| Sodium cyclamate | 20 g |
| Sucrose palmitate | 2 g |
| Hydroxypropylmethyl cellulose | 5 g |

Other Ingredients:

| | |
|---|---|
| Calcium acetate (according to the requirements of the European Pharmacopoeia), granulated (Paul Lohmann) | 435 g |
| Heavy magnesium carbonate (according to the requirements of the European Pharmacopoeia), granulated with approximately 10% cornstarch (magnesium carbonate DC90 S/C Paul Lohmann) | 262 g |
| Aspartame | 10 g |
| Sorbitol | 200 g |
| Xylitol | 136 g |
| Orange flavoring | 30 g |

For the effervescent granules, citric acid, monosodium citrate, sodium bicarbonate, sodium cyclamate, sucrose palmitate and hydroxypropyl cellulose are mixed in a Diosna mixer with a 1-liter container and sprayed slowly with 5 g ethanol through a nozzle while stirring. Next granulation is continued for 10 minutes. Then the composition is spread on a metal sheet and dried for 60 minutes in a vacuum drying cabinet at 30° C. and a final pressure of <50 mbar.

The resulting effervescent granules are pressed through a 1 mm screen and mixed with the other ingredients in a 5-liter cube mixer.

The mixture is welded into an aluminum stickpack in portions of 1400 mg.

Example 3

A granular preparation with 167 mg calcium per dose can be prepared by the following method:

| | |
|---|---|
| Calcium acetate (according to the requirements of the European Pharmacopoeia), granulated (Paul Lohmann) | 660 g |
| Aspartame | 10 g |
| Sorbitol | 200 g |
| Xylitol | 100 g |
| Orange flavoring | 30 g |
| Finished effervescent granules from Example 2 | 200 g |

All the ingredients are mixed in a 5-liter cube mixer. The mixture is welded into an aluminum stickpack in portions of 1200 mg each.

Example 4

A granular preparation with 167 mg calcium per dose can also be prepared by the following method:
Calcium Acetate with a Taste-Masking Coating:

| | |
|---|---|
| Calcium acetate (according to the requirements of the European Pharmacopoeia), granulated (Paul Lohmann) | 1980 g |
| Glycerol palmitostearate (Precirol® ATO 5, Gattefosse) | 220 g |

Other Ingredients:

| | |
|---|---|
| Aspartame | 30 g |
| Sorbitol | 600 g |
| Xylitol | 320 g |
| Orange flavoring | 100 g |
| Finished effervescent granules from Example 2 | 650 g |

The calcium acetate is moved in a fluidized bed apparatus (Unilab 05 from Hüttlin) at an inlet air temperature of 35° C. and coated at a spray rate of 6 g/min with a melt of glycerol palmitostearate heated to 80° C. and atomized through a spray nozzle of 1 mm at an atmospheric pressure of 1 bar by means of spray air heated to 60° C. Then the coated granulates are cooled to 25° C. for 10 minutes in the ball coater.

The coated calcium acetate is passed through a 2 mm screen, mixed with the other ingredients in a 10-liter cube mixer and then welded in aluminum stickpacks in portions of 1300 mg each.

Example 5

A granular preparation with 220 mg calcium and 120 mg magnesium per dose can be prepared by the following method:

| | |
|---|---|
| Calcium acetate from Example 4 with a taste-masking coating (calcium acetate content 90%) | 1450 g |
| Heavy magnesium carbonate (according to the requirements of the European Pharmacopoeia), granulated with approximately 10% cornstarch (magnesium carbonate DC90 S/C Paul Lohmann) | 785 g |
| Aspartame | 30 g |
| Sorbitol | 600 g |
| Xylitol | 400 g |
| Orange flavoring | 100 g |
| Finished effervescent granules from Example 2 | 625 g |

All the ingredients are mixed in a 10-liter cube mixer and welded into aluminum stickpacks in portions of 2660 mg each.

Example 6

A granular preparation with 220 mg calcium and 120 mg magnesium per dose can be prepared by the following method:

| | |
|---|---|
| Calcium acetate from Example 4 with a taste-masking coating (calcium acetate content 90%) | 1450 g |
| Heavy magnesium carbonate (according to the requirements of the European Pharmacopoeia), granulated with approximately 10% cornstarch (magnesium carbonate DC90 S/C Paul Lohmann) | 785 g |
| Aspartame | 30 g |
| Sorbitol | 550 g |
| Xylitol | 400 g |
| Sodium carboxymethyl cellulose | 50 g |
| Orange flavoring | 100 g |
| Finished effervescent granules from Example 2 | 625 g |

All the ingredients are mixed in a 10-liter cube mixer and welded into aluminum stickpacks in portions of 2660 mg.

Example 7

The finished mixture from Example 4 can be filled into stickpacks of a corresponding filling volume (adaptable through the width and especially the length of the stickpacks) in the following portions to prepare different calcium doses:

| Calcium dose | Corresponding weight of calcium acetate (anhydrous) | Filling amount of stickpacks |
|---|---|---|
| 50 mg | 198 mg | 389 mg |
| 100 mg | 395 mg | 778 mg |
| 150 mg | 593 mg | 1168 mg |
| 200 mg | 791 mg | 1557 mg |
| 250 mg | 988 mg | 1946 mg |
| 300 mg | 1186 mg | 2335 mg |
| 350 mg | 1384 mg | 2725 mg |
| 400 mg | 1582 mg | 3114 mg |
| 500 mg | 1977 mg | 3892 mg |

Example 8

A granular preparation with 220 mg calcium and 110 mg magnesium per dose can be prepared by the following method:

| | |
|---|---|
| Calcium acetate from Example 4 with a taste-masking coating (calcium acetate content 90%) | 1450 g |
| Heavy magnesium carbonate (according to the requirements of the European Pharmacopoeia), granulated, with approximately 10% cornstarch (magnesium carbonate DC90 S/C Paul Lohmann) | 720 g |
| Aspartame | 30 g |
| Sorbitol | 550 g |
| Xylitol | 375 g |
| Sodium carboxymethyl cellulose | 50 g |
| Orange flavoring | 100 g |
| Finished effervescent granules from Example 2 | 625 g |

All the ingredients are mixed in a 10-liter cube mixer and welded into aluminum stickpacks in portions of 2600 mg each.

Example 9

The finished mixture from Example 8 can be filled into stickpacks of a corresponding filling volume (adjustable through the width and especially the length of the stickpacks) to produce different doses of calcium and magnesium in the following portions, each in a 2:1 ratio (Ca:Mg):

| Calcium dose | Magnesium dose | Filling amount of stickpacks |
|---|---|---|
| 50 mg | 25 mg | 591 mg |
| 100 mg | 50 mg | 1182 mg |
| 150 mg | 75 mg | 1773 mg |
| 200 mg | 100 mg | 2364 mg |
| 250 mg | 125 mg | 2955 mg |
| 300 mg | 150 mg | 3545 mg |
| 350 mg | 175 mg | 4136 mg |

Example 10

The finished mixture from Example 4 can be used to produce different calcium doses with different dosing ratios of calcium to magnesium. This yields the following filling quantities in stickpacks of a corresponding filling volume (adjustable through the width and especially the length of the stickpacks):

| Ca:Mg ratio | Calcium dose | Magnesium dose | Corresponding weight of the mixture from Example 4 to be used per stickpack for calcium | Corresponding weight of magnesium carbonate DC90 S/C to be used for magnesium per stickpack | Filling amount of the stickpacks |
|---|---|---|---|---|---|
| 4:1 | 100 mg | 25 mg | 778 mg | 28 mg | 806 mg |
| 2:1 | 100 mg | 50 mg | 778 mg | 56 mg | 834 mg |
| 1:1 | 100 mg | 100 mg | 778 mg | 111 mg | 889 mg |
| 3:1 | 150 mg | 50 mg | 1168 mg | 56 mg | 1224 mg |
| 2:1 | 150 mg | 75 mg | 1168 mg | 83 mg | 1251 mg |
| 1.5:1 | 150 mg | 100 mg | 1168 mg | 111 mg | 1279 mg |
| 4:1 | 200 mg | 50 mg | 1557 mg | 56 mg | 1613 mg |
| 2:1 | 200 mg | 100 mg | 1557 mg | 111 mg | 1668 mg |
| 1.33:1 | 200 mg | 150 mg | 1557 mg | 167 mg | 1724 mg |
| 1:1 | 200 mg | 200 mg | 1557 mg | 222 mg | 1779 mg |
| 5:1 | 250 mg | 50 mg | 1946 mg | 56 mg | 2002 mg |
| 2.5:1 | 250 mg | 100 mg | 1946 mg | 111 mg | 2057 mg |
| 2:1 | 250 mg | 125 mg | 1946 mg | 139 mg | 2085 mg |
| 1.67:1 | 250 mg | 150 mg | 1946 mg | 167 mg | 2113 mg |
| 1:1 | 250 mg | 250 mg | 1946 mg | 278 mg | 2224 mg |
| 3:1 | 300 mg | 100 mg | 2335 mg | 111 mg | 2446 mg |
| 2:1 | 300 mg | 150 mg | 2335 mg | 167 mg | 2502 mg |
| 1.5:1 | 300 mg | 200 mg | 2335 mg | 222 mg | 2557 mg |
| 1:1 | 300 mg | 300 mg | 2335 mg | 333 mg | 2668 mg |

Example 11

A granular preparation with 167 mg calcium per dose can also be prepared by the following method:

Calcium Acetate with a Taste-Masking Coating:

| | |
|---|---|
| Calcium acetate (according to the requirements of the European Pharmacopoeia), granulated (Paul Lohmann) | 1980 g |
| Basic butylated methacrylate copolymer, Ph. Eur. (Eudragit EPO ®, Evonik) | 400 g |
| Sodium dodecyl sulfate | 40 g |
| Stearic acid | 60 g |
| Talc | 160 g |

Other Ingredients:

| | |
|---|---|
| Aspartame | 30 g |
| Sorbitol | 600 g |
| Xylitol | 320 g |
| Orange flavoring | 100 g |
| Finished effervescent granules from Example 2 | 810 g |

First, a film coating suspension with an excess of 25% is added to the ingredients of the coating material as listed above. The excess covers the spray losses during production so that the planned quantity of a coating of 20% methacrylate polymer can be applied. To do so, first 50 g sodium dodecyl sulfate is dissolved in 3.5 L of purified water at room temperature (approximately 20° C.). After 5 minutes, 75 g stearic acid is dispersed in the solution while stirring further using an UltraTurrax. After another 5 minutes, 500 g Eudragit EPO is distributed in the dispersion while stirring further and is further dispersed for 30 minutes intensely using the UltraTurrax. In parallel, 200 g talc is dispersed in 1.5 L purified water at room temperature (approximately 20° C.) while stirring with an UltraTurrax and then stirring is continued intensely for 20 minutes more. The two dispersions are mixed together and then applied to the granulated calcium acetate by means of a fluidized bed device with a Wurster insert (Glatt GCPG2 LabSystem) in the bottom spray method. The dispersions are applied in two partial batches, each using half of the materials. The inlet air temperature is set at approximately 50° C., so that a product temperature of approximately 30° C. is established during film coating. The suspension is applied to the calcium acetate through a 1.2 mm nozzle at an air pressure of approximately 1.5 bar and at a feed rate of 10 g per minute. The process is terminated when the weight of the granules has increased by approximately 33%. The coated granules from the two partial batches is passed through a 2 mm screen and mixed with the other ingredients in a 10 liter cube mixer and then welded in aluminum stickpacks in portions of 1500 mg each.

Example 12

A granular preparation with 110 mg calcium and 60 mg magnesium per dose can be prepared by the following method:

| | |
|---|---|
| Calcium acetate from Example 11 with a taste-masking coating (calcium acetate content 75%) | 1740 g |
| Heavy magnesium carbonate (according to the requirement of the European Pharmacopoeia), granulated with approximately 10% cornstarch (magnesium carbonate DC90 S/C Paul Lohmann) | 785 g |
| Aspartame | 30 g |
| Sorbitol | 600 g |
| Xylitol | 400 g |
| Orange flavoring | 100 g |
| Finished effervescent granules from Example 2 | 695 g |

All the ingredients are mixed in a 10-liter cube mixer and welded in aluminum stickpacks in portions of 1450 mg each.

Example 13

A granular preparation with 220 mg calcium and 120 mg magnesium per dose can be packaged in aluminum stickpacks by filling the finished mixture from Example 12 into aluminum stickpacks in portions of 2900 mg each.

Example 14

A preparation containing 125 mg lanthanum (=238.5 mg lanthanum hydroxycarbonate) per dose can be prepared by the following method:

| | |
|---|---|
| Lanthanum hydroxycarbonate (lanthanum content 52.4%) | 715 g |
| Aspartame | 10 g |
| Sorbitol | 200 g |
| Xylitol | 100 g |
| Orange flavoring | 30 g |
| Finished effervescent granules from Example 2 | 220 g |

All the ingredients are mixed in a 5-liter cube mixer. The mixture is welded in an aluminum stickpack in portions of 425 mg each.

Example 15

Preparations containing 250 mg, 500 mg, 750 mg and 1000 mg lanthanum per dose can be obtained by filling the mixture from Example 14 into aluminum stickpacks according to the following table:

| Lanthanum dose | Corresponding weight of lanthanum hydroxycarbonate | Filling amount of stickpacks with finished mixture from Example 14 |
|---|---|---|
| 250 mg | 477 mg | 850 mg |
| 500 mg | 954 mg | 1700 mg |
| 750 mg | 1431 mg | 2550 mg |
| 1000 mg | 1908 mg | 3400 mg |

Example 16

A preparation with 800 mg sevelamer hydrochloride per dose can be prepared by the following method:

| | |
|---|---|
| Sevelamer hydrochloride, dried | 800 g |
| Aspartame | 10 g |
| Sorbitol | 200 g |
| Xylitol | 100 g |
| Orange flavoring | 40 g |
| Finished effervescent granules from Example 2 | 250 g |

All the ingredients are mixed in a 5-liter cube mixer. The mixture is welded in an aluminum stickpack in portions of 1400 mg each.

Example 17

Preparations with 1600 mg and 2400 mg sevelamer per dose can be packaged in aluminum stickpacks by filling the mixture from Example 16 into aluminum stickpacks according to the following table:

| Sevelamer dose | Filling amount of stickpacks with finished mixture from Example 16 |
|---|---|
| 1600 mg | 2800 mg |
| 2400 mg | 4200 mg |

Example 18

A preparation with 800 mg sevelamer hydrochloride per dose can be prepared by the following method:

| | |
|---|---|
| Sevelamer hydrochloride, dried | 800 g |
| Povidone K30 | 50 g |
| Aspartame | 10 g |
| Sorbitol | 200 g |
| Xylitol | 100 g |
| Orange flavoring | 40 g |
| Finished effervescent granules from Example 2 | 250 g |

Povidone K30 is dissolved in 150 mL of a mixture of 90% ethanol and 10% purified water. Sevelamer hydrochloride is granulated with the povidone solution in a fluidized bed granulator (Glatt GCPG2 LabSystem) in the top spray method. The granules are passed through a 1 mm screen and mixed with the other ingredients in a 5-liter cube mixer. The mixture is welded in an aluminum stickpack in portions of 1450 mg each.

The invention claimed is:
1. A pharmaceutical composition for treating a renally insufficient patient having hyperphosphatemia comprising untableted granules having a phosphate binding core with a taste-masking coating thereon,
   a) the coating containing at least one effervescent agent comprising magnesium carbonate and a solid organic edible acid or acidic salt thereof, wherein the solid organic edible acid is selected from the group consisting of citric acid, tartaric acid, malic acid, adipic acid, succinic acid, fumaric acid, ascorbic acid, and maleic acid, and
   b) the core containing, at a weight ratio of 1:1 to 4:1, calcium acetate and magnesium carbonate as phosphate binding substance, wherein calcium acetate and magnesium carbonate combined constitute 15-80% of the weight of the composition,
wherein the granules have an average particle size of 100-3500 μm.

2. The composition of claim 1, wherein the coating is a spray coating.

3. The composition of claim 1, wherein the coating is a melt coating.

4. The composition of claim 1, wherein the coating is a spray coating of suspensions and/or solutions.

5. The composition of claim 1, wherein the granules further contain at least one sugar alcohol.

6. The composition of claim 1, wherein the effervescent agent constitutes 3-60% of the weight of the composition.

7. The composition of claim 1 in the form of a unit dose containing 0.5-5 g of the granules.

8. The composition of claim 1, in the form of a stickpack containing 0.5-4 g of the granules.

\* \* \* \* \*